US010359342B2

(12) United States Patent
Stolz et al.

(10) Patent No.: US 10,359,342 B2
(45) Date of Patent: Jul. 23, 2019

(54) PIPELINE SAMPLER

(71) Applicant: Sentry Equipment Corp., Oconomowoc, WI (US)

(72) Inventors: Eric Stolz, Milwaukee, WI (US); David Nowak, St. Francis, WI (US)

(73) Assignee: Sentry Equipment Corp., Oconomowoc, WI (US)

( * ) Notice: Subject to any disclaimer, the term of this patent is extended or adjusted under 35 U.S.C. 154(b) by 164 days.

(21) Appl. No.: 15/459,247

(22) Filed: Mar. 15, 2017

(65) Prior Publication Data

US 2018/0266921 A1   Sep. 20, 2018

(51) Int. Cl.
| | | |
|---|---|---|
| *G01N 1/04* | (2006.01) | |
| *G01N 1/14* | (2006.01) | |
| *G01N 1/16* | (2006.01) | |
| *G01N 1/20* | (2006.01) | |

(52) U.S. Cl.
CPC ............. *G01N 1/2035* (2013.01); *G01N 1/04* (2013.01); *G01N 1/14* (2013.01); *G01N 1/16* (2013.01); *G01N 2001/2057* (2013.01)

(58) Field of Classification Search
CPC ......... G01N 1/2035; G01N 2001/2057; G01N 1/20; G01N 2001/1025; G01N 17/046; G01N 1/04; G01N 1/10; G01N 1/14; G01N 1/22; G01N 2001/105; G01N 2001/1427; G01N 2001/205; G01N 27/283; G01N 30/02; G01N 35/1079; G01N 7/00; G01F 15/185; G01F 15/00; F17D 3/10; G01K 13/02; G01K 1/146; G01L 19/0007; G01L 7/00
See application file for complete search history.

(56) References Cited

U.S. PATENT DOCUMENTS

| 3,308,669 A | 3/1967 | Grise et al. |
| 4,082,004 A | 4/1978 | Weber et al. |
| (Continued) | | |

FOREIGN PATENT DOCUMENTS

DE   102013102199 A1   9/2014

OTHER PUBLICATIONS

International Search Report and Written Opinion. PCT Application No. PCT/US2018/022355, dated May 10, 2018. 8 pages.

*Primary Examiner* — Randy W Gibson
*Assistant Examiner* — Gedeon M Kidanu
(74) *Attorney, Agent, or Firm* — Jansson Munger McKinley & Kirby Ltd.

(57) ABSTRACT

An apparatus for collecting a dry material sample flowing in a duct is disclosed. The apparatus includes a sample tube having a closed distal end and a sample-inlet aperture in the wall of the sample tube adjacent the closed distal end, a housing configured as a fluid cylinder with a duct end and an outlet end and a piston mounted around and connected to the sample tube and positioned within the housing. The apparatus also includes first and second sealing sleeves around and slideably supporting the sample tube. The duct end includes the first sealing sleeve and the outlet end includes the second sealing sleeve. A duct-connecting structure extends between the duct end of the housing and the duct. The sample tube is a piston rod within the fluid-cylinder housing, and the fluid-cylinder housing is configured to extend and retract the sample tube within the duct.

8 Claims, 11 Drawing Sheets

(56) References Cited

U.S. PATENT DOCUMENTS

| | | | | |
|---|---|---|---|---|
| 4,433,587 | A | * | 2/1984 | Risdal .................. G01N 1/2035 73/863.52 |
| 4,562,747 | A | | 1/1986 | Jaeger |
| 4,562,749 | A | * | 1/1986 | Clark .................... G01N 1/2035 73/863.84 |
| 4,631,967 | A | * | 12/1986 | Welker ................. G01F 15/185 73/861.25 |
| 5,138,755 | A | | 8/1992 | Evans et al. |
| 5,406,855 | A | * | 4/1995 | Welker ................. G01N 1/2035 73/863.83 |
| 6,055,870 | A | * | 5/2000 | Jaeger ...................... G01N 1/04 73/863.83 |
| 6,338,359 | B1 | * | 1/2002 | Welker ...................... F17D 3/10 137/15.12 |
| 6,357,306 | B1 | * | 3/2002 | Jaeger .................. G01N 1/2035 73/863.83 |
| 6,357,470 | B1 | | 3/2002 | Evans et al. |
| 6,827,486 | B2 | * | 12/2004 | Welker .................... G01K 13/02 374/147 |
| 6,886,420 | B2 | * | 5/2005 | Handel ................. G01N 1/2035 73/863.83 |
| 6,964,517 | B2 | | 11/2005 | Welker |
| 7,481,124 | B2 | * | 1/2009 | Schadt ................. G01N 1/2035 73/863.86 |
| 7,886,624 | B1 | * | 2/2011 | Mayeaux ............. G01N 1/2035 73/866.5 |
| 8,087,308 | B2 | | 1/2012 | Gauthier et al. |
| 8,312,780 | B2 | * | 11/2012 | Blacklin ................. B01L 3/021 73/863 |
| 9,194,773 | B2 | * | 11/2015 | Najrani ................ G01N 1/2035 |

\* cited by examiner

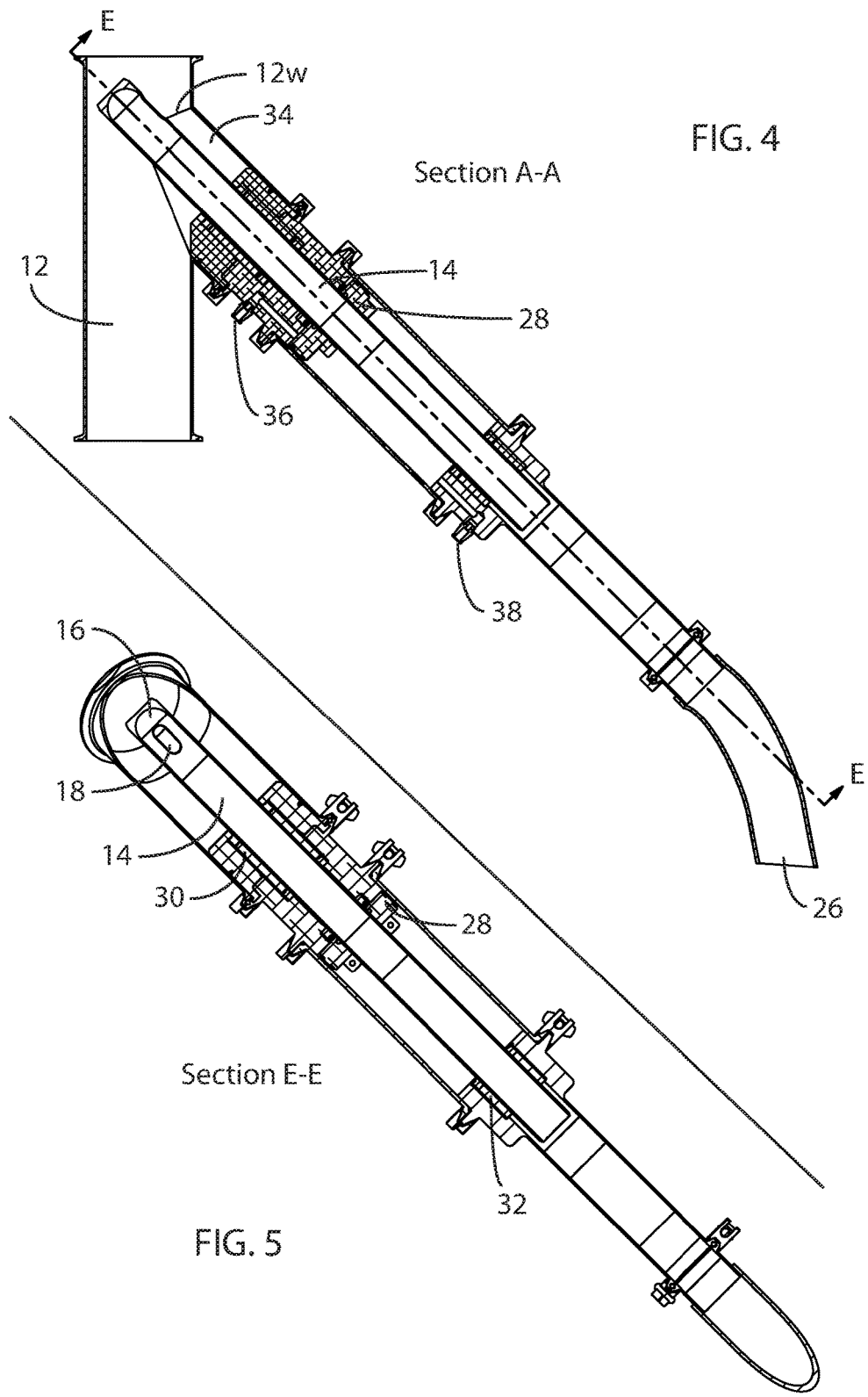

Section F-F

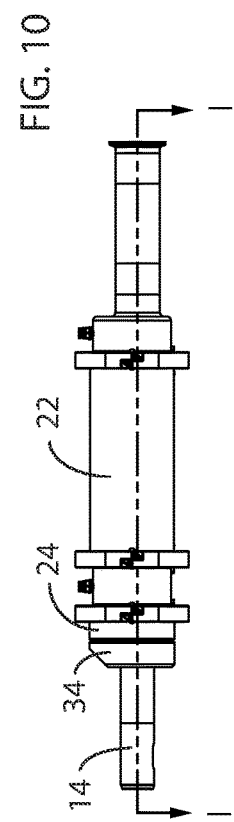
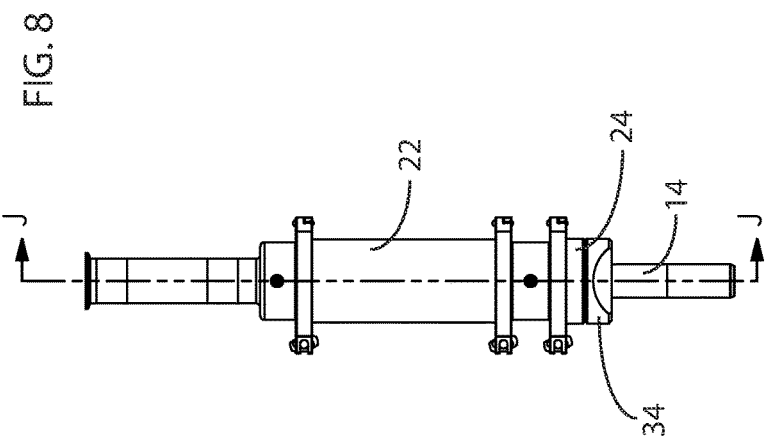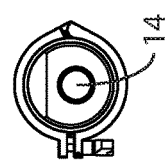

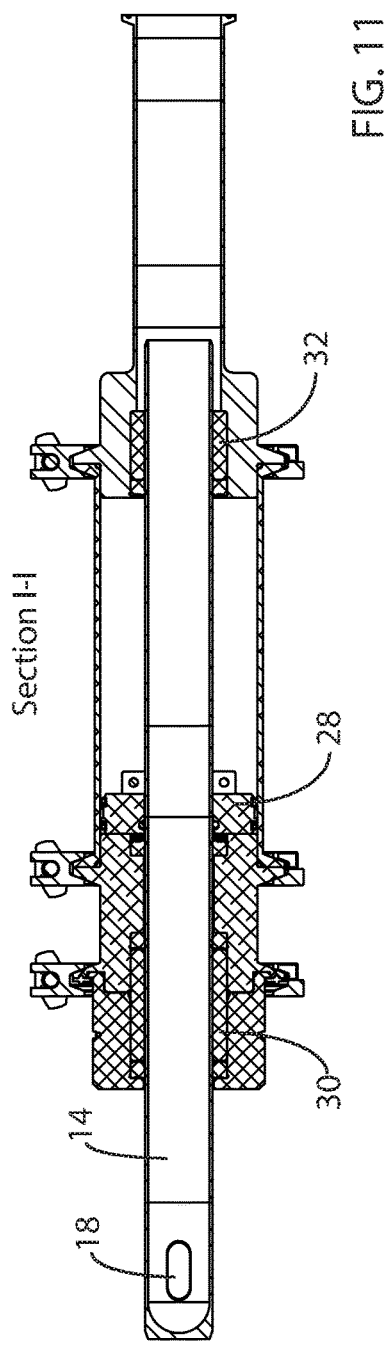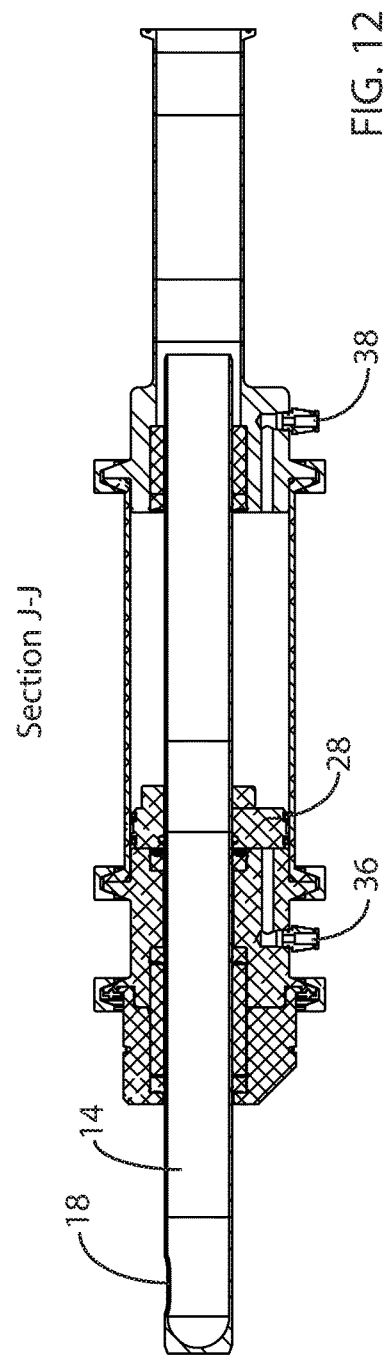

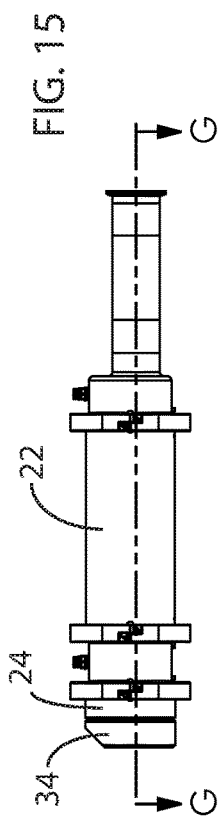
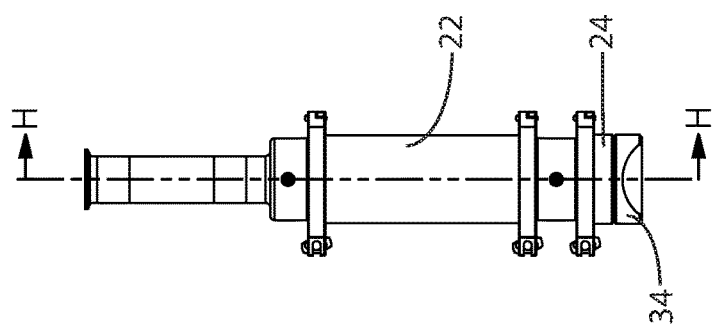
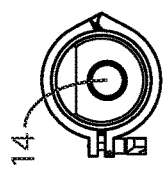

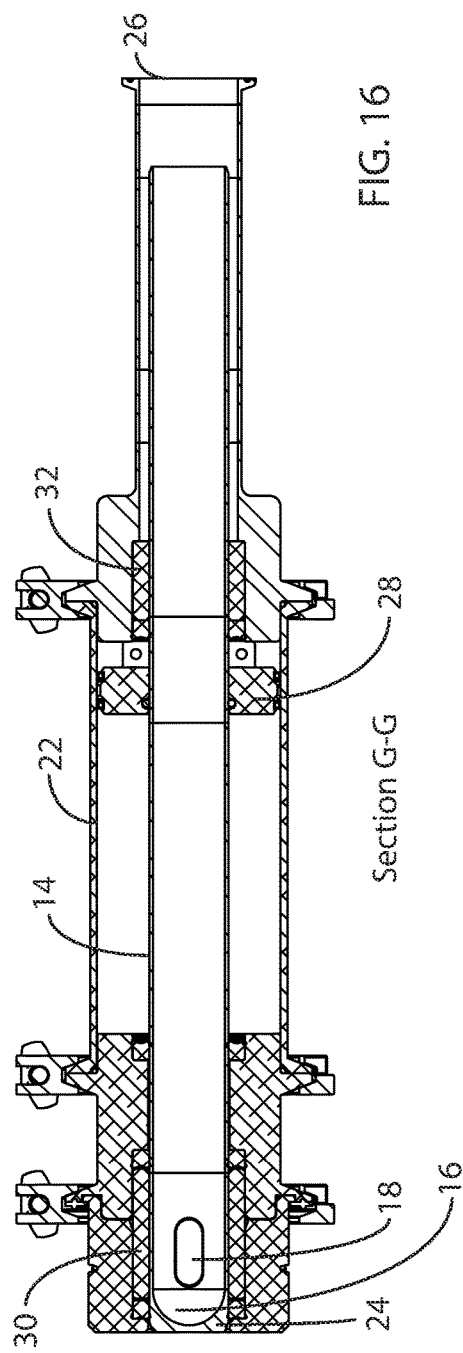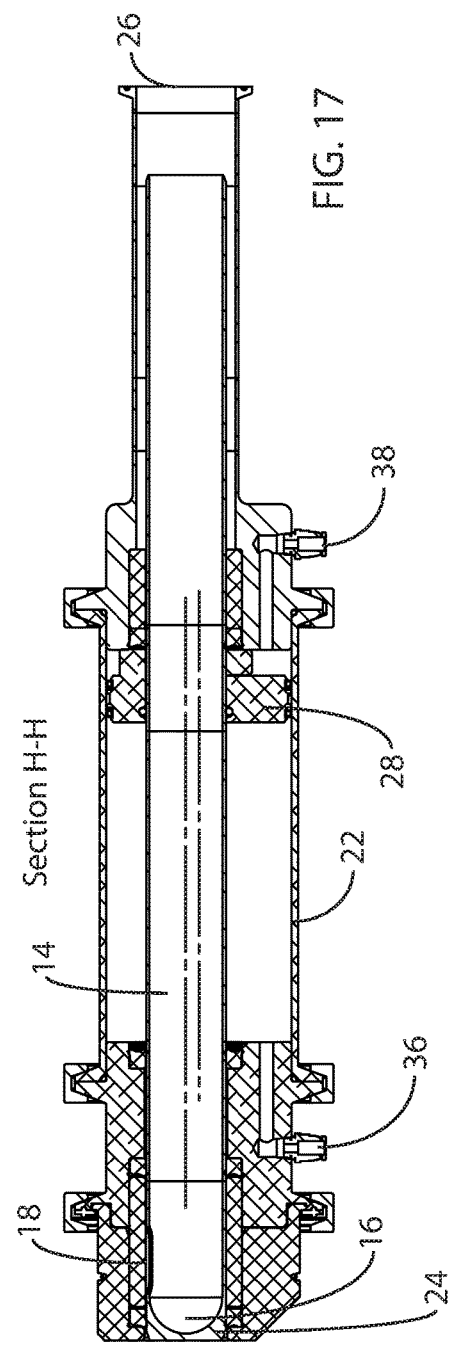

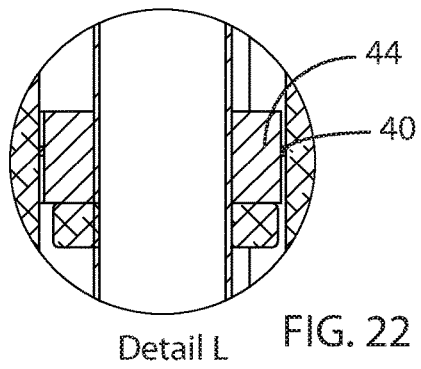
Detail L    FIG. 22
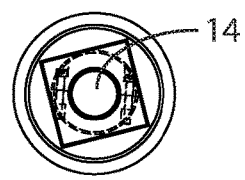
FIG. 23
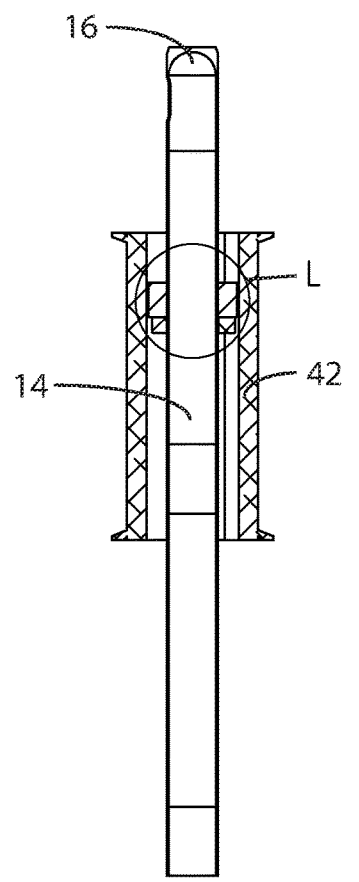
FIG. 21
Section K-K
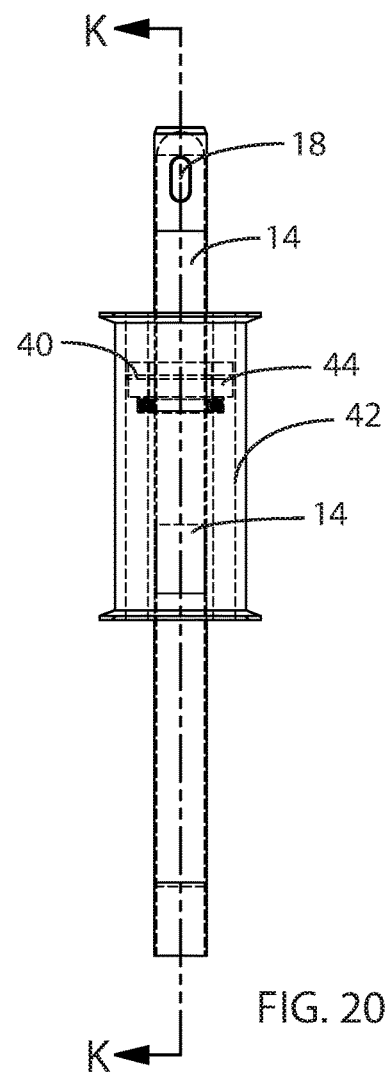
FIG. 20

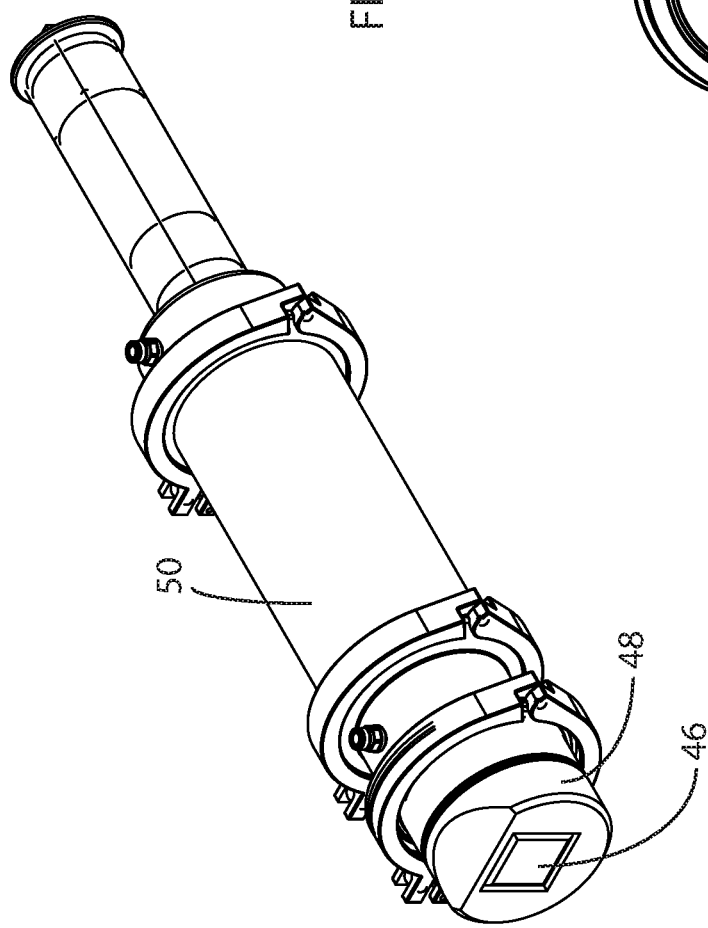
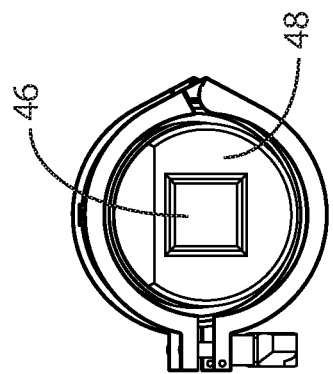

PIPELINE SAMPLER

FIELD OF THE INVENTION

The present invention generally relates to a sampler for sampling processes that convey bulk solid and friable powder, and more particularly, to a single-piece sampling apparatus with an anti-rotation configuration.

BACKGROUND OF THE INVENTION

A variety of systems for sampling various materials are known. However, numerous disadvantages and shortcomings exist with prior systems, and there is a need for improvement to overcome such disadvantages and shortcomings. Some examples of sampling devices of the prior art are disclosed in U.S. Pat. Nos. 4,433,587 and 4,082,004.

The sampling systems of the prior art have several drawbacks. Some such drawbacks are that the sampling systems of the prior art have numerous functioning parts which can lead to the use of higher-cost components and to longer assembly times. It would be preferable to have a sampling device which has fewer components such as a body which functions as both the process tube and air cylinder. It would also be preferable to have a sampling device which includes an offset tube as well as an air cylinder piston which prevents rotation of the tube and maintains the aperture in proper alignment with process flow. It would also be preferable to have a sampling device that requires few or no tools to assemble or disassemble as well as clean and maintain.

In processes that convey bulk solid and friable powder media in a process pipeline (or process tube), there is a need to extract a sample of the process medium without affecting the material properties. Current samplers employ a tube that extends into the process pipeline (or process tube) and an aperture on the side of the tube which then allows process media to enter the sampler. The process media then are allowed to travel through the tube and be collected in a receptacle. The tube is then retracted from the process pipeline. Proper extraction of the sample requires the aperture of the sampling tube to be facing in the direction of flow of the process medium. Currently, there are a number of methods to ensure rotational alignment which generally include the use of fixtures, effectors and apertures on pneumatic cylinders attached to sample extraction devices. These include using anti-rotation pins, dual piston rods, linkages and dual support bars. All of these methods involve the added complexity of extra parts, seals and wear points. It is to these needs that this inventive sampling apparatus or device is drawn.

The present device uses a sample conveyance tube with an aperture that allows the process media to enter the tube. The device ensures the aperture maintains proper orientation to the medium flow. The invention allows for extraction of a sample while maintaining aperture orientation to the flow. The inventive apparatus also reduces the number of parts, and therefore the complexity, making it easier to clean and maintain.

The present device maintains simplicity by lowering the part count while providing the critical anti-rotation feature. This is a novel improvement because it maintains the basic shape and form of the air cylinder while still preventing rotation through the offset piston and rod axes and allowing the piston rod in the cylinder to function as the sample conveyance tube. This is a substantial improvement over the samplers of the prior art.

It is to all the above-noted needs that the device of this application is drawn. This invention addresses and overcomes such problems.

OBJECTS OF THE INVENTION

An object of the present invention is to provide an improved pipeline-sampling apparatus in which the process tube and air cylinder are the same structure.

Another object of this invention is to provide an improved pipeline-sampling apparatus which has fewer and lower-cost components.

Yet another object of this invention is to provide an improved pipeline-sampling apparatus which requires few or no tools to assemble/disassemble as well as clean and maintain.

Another object of the invention is to provide an improved pipeline-sampling apparatus which overcomes certain problems of existing devices and methods of the prior art.

SUMMARY OF THE INVENTION

The present invention relates to an improved apparatus for collecting a dry material sample flowing in a duct. The apparatus includes a sample tube having a closed distal end and a sample-inlet aperture in the wall of the sample tube adjacent the closed distal end, a housing configured as a fluid cylinder and having a duct end and an outlet end, a piston mounted around and connected to the sample tube and positioned within the housing, first and second sealing sleeves around and slideably supporting the sample tube, the duct end including the first sealing sleeve and the outlet end including the second sealing sleeve, and a duct-connecting structure extending between the duct end of the housing and the duct. The sampling tube is a piston rod within the fluid-cylinder housing, and the fluid-cylinder housing is configured to extend and retract the sample tube within the duct.

It is highly preferable that the fluid cylinder is an air cylinder. In preferred embodiments, the duct-connecting structure is welded to the duct and the duct end includes a retract fluid inlet to the fluid cylinder. Preferably, the outlet end includes an extend fluid inlet to the cylinder.

In some preferred embodiments, the sample tube and fluid cylinder housing have centerlines which are not coextensive. In other preferred embodiments, the piston and fluid-cylinder have non-circular cross-sections to prevent rotation of the piston in the cylinder.

It is preferable that the first and second sealing sleeves include non-circular seals and the sample tube is non-circular, configured to sealingly slide within the non-circular seals.

BRIEF DESCRIPTION OF THE DRAWINGS

The drawings illustrate a preferred embodiment including the above-noted characteristics and features of the invention. The invention will be readily understood from the descriptions and drawings. In the drawings:

FIG. 4 is a cross-sectional view taken along line A-A of FIG. 3;

FIG. 5 is a cross-sectional view taken along line E-E of FIG. 4;

FIG. 8 is a front view of a pipeline apparatus of FIG. 1 with the sampling tube extended but without the pipeline shown;

FIG. 9 is a top view of the pipeline apparatus of FIG. 8;

FIG. 10 is a side view of the pipeline apparatus of FIG. 8;

FIG. 11 is a cross-sectional view taken along line I-I of FIG. 10;

FIG. 12 is a cross-sectional view taken along line J-J of FIG. 8;

FIG. 13 is a front view of a pipeline apparatus of FIG. 8 with the sampling tube retracted;

FIG. 14 is a top view of the pipeline apparatus of FIG. 13;

FIG. 15 is a side view of the pipeline apparatus of FIG. 13;

FIG. 16 is a cross-sectional view taken along line G-G of FIG. 15;

FIG. 17 is a cross-sectional view taken along line H-H of FIG. 13;

FIG. 20 is a cutaway view of the pipeline apparatus of FIG. 18;

FIG. 21 is a cross-sectional view taken along line K-K of FIG. 20;

FIG. 22 is a detailed view of Section B of the pipeline apparatus of FIG. 21;

FIG. 23 is an end view of the pipeline apparatus of FIG. 18;

FIG. 24 is a perspective view of a third embodiment of the inventive pipeline apparatus for collecting a dry material sample flowing in a duct; and FIG. 25 is an end view of the pipeline apparatus of FIG. 24.

DETAILED DESCRIPTION OF PREFERRED EMBODIMENTS

The inventive sampler apparatus maintains alignment of the sample tube aperture to the product flow in a pressurized dry material product process line and uses the sample conveyance tube itself as the piston rod of a pneumatic (or alternatively, hydraulic) cylinder. The inventive apparatus combines the sampling tube with the air cylinder used to actuate it, thereby further reducing the overall parts count and complexity. Instead of mechanically preventing rotation of the aperture via a restriction on the air cylinder and effector, the device incorporates the air cylinder, anti-rotation structure and sample conveyance tube into a single apparatus. FIGS. 1-25 illustrate embodiments of such inventive apparatus used for collecting a dry material sample flowing in a duct 12.

Figure 1:
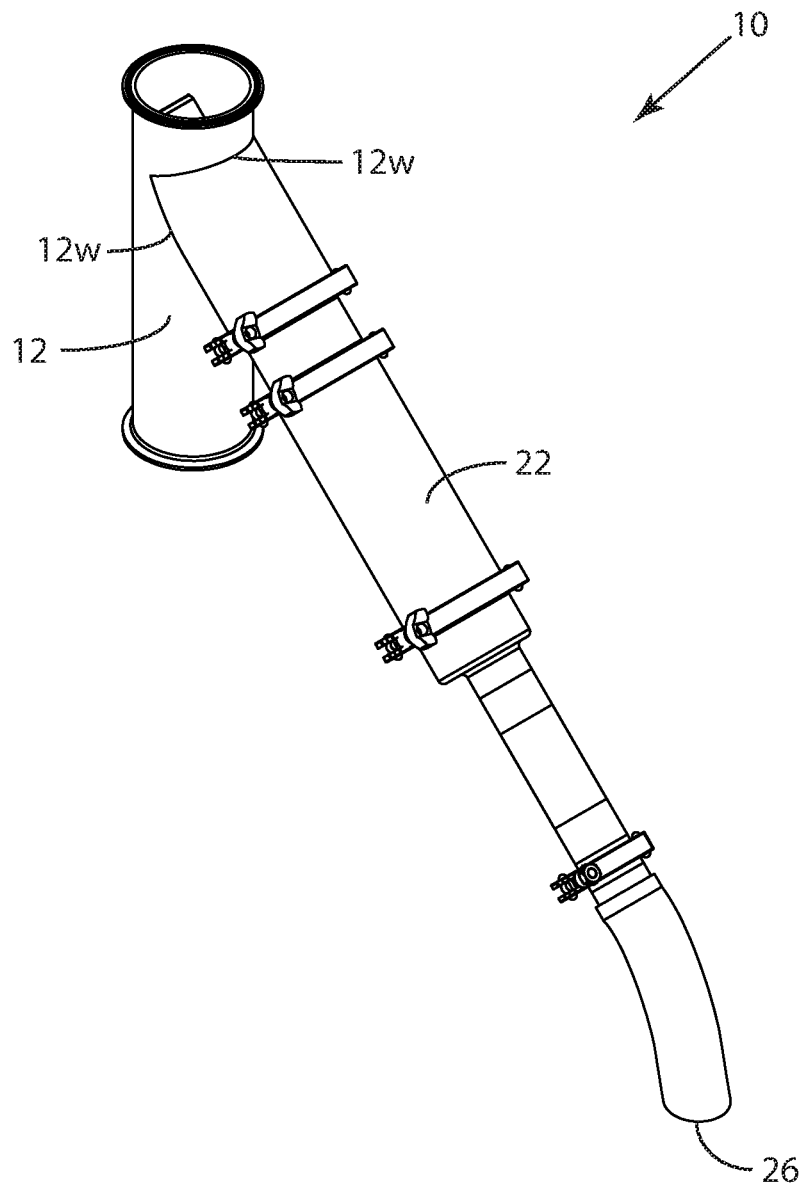
FIG. 1 is a front perspective view of an embodiment of the inventive pipeline apparatus for collecting a dry material sample flowing in a duct.
Figure 2:
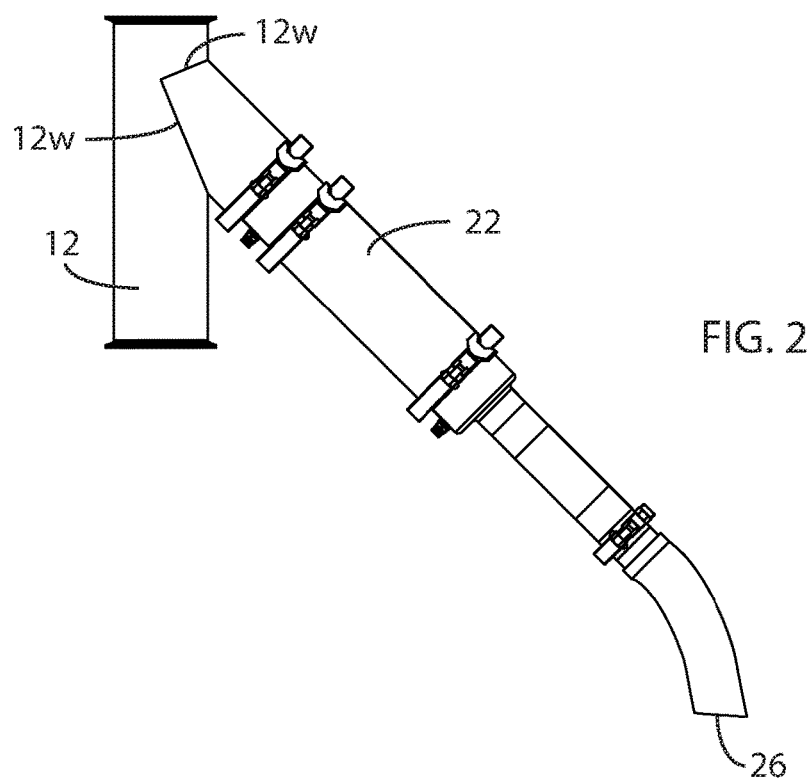
FIG. 2 is a side view of the pipeline apparatus of FIG. 1 with the sampling tube in an extended position.
Figure 3:
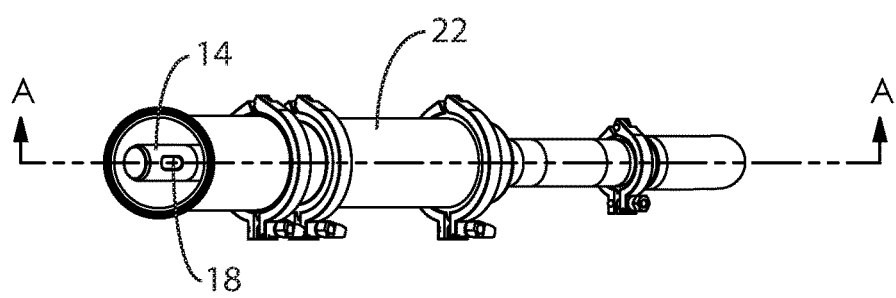
FIG. 3 is a perspective view of the pipeline apparatus of FIG. 1 illustrating the inlet sample aperture.

An embodiment 10 of the inventive apparatus, as illustrated in FIGS. 1-17, includes a sample tube 14 having a closed distal end 16 and a sample-inlet aperture 18 in the wall of sample tube 14 adjacent closed distal end 16. FIGS. 1-3 illustrate that apparatus 10 also includes a housing configured as a fluid cylinder 22 which has a duct end 24 and an outlet end 26. A piston 28 is mounted around and connected to sample tube 14 and positioned within housing 22. First and second sealing sleeves 30, 32 are around and slideably supporting sample tube 14. Duct end of fluid cylinder 24 includes first sealing sleeve 30 and outlet end of fluid cylinder 26 includes second sealing sleeve 32. As can be seen best in FIGS. 4 and 7, a duct-connecting structure 34 extends between duct end 24 of housing 22 and duct 12.

FIGS. 1-25 illustrate that fluid cylinder 22 is an air cylinder. In the inventive apparatus 10, sample tube 14 and fluid-cylinder housing 22 have centerlines which are not coextensive.

Figure 7:
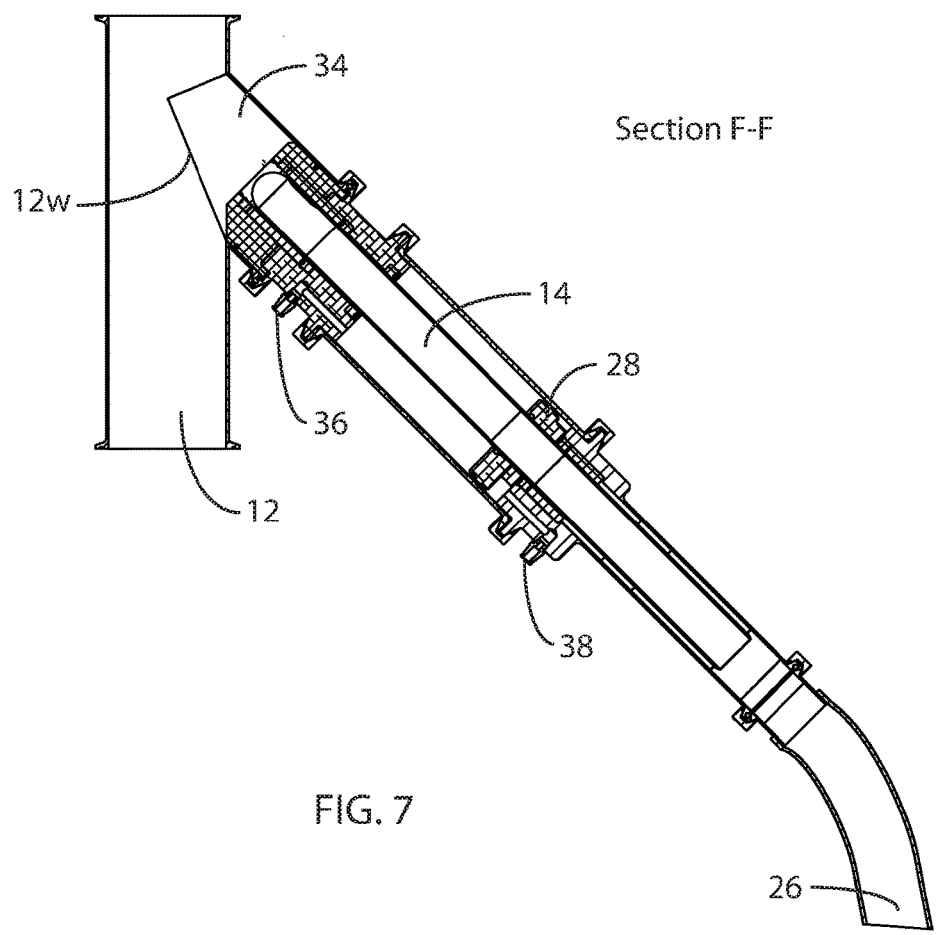
FIG. 7 is a cross-sectional view taken along line F-F of FIG. 6.

FIGS. 1, 2, 4 and 7 all illustrate that duct-connecting structure 34 is welded to duct 12 by a weld 12w. Duct end 24 includes a retract fluid inlet 36 to fluid cylinder 22. FIGS. 4 and 7 illustrate best that outlet end 26 includes an extend fluid inlet 38 to fluid cylinder 22.

In apparatus 10, sample tube 14 is a piston 28 rod within fluid-cylinder housing 22, and fluid-cylinder housing 22 is configured to extend and retract sample tube 14 within duct 12. FIG. 4 shows sample tube 14 in an extended state and in duct 12 collecting a sample. FIG. 5 illustrates sample tube 14 in a retracted state. FIG. 5 specifically also illustrates closed distal end 16 and sample inlet aperture 18 of sample tube 14. Piston 28 is also easily visible in FIG. 5.

Figure 6:
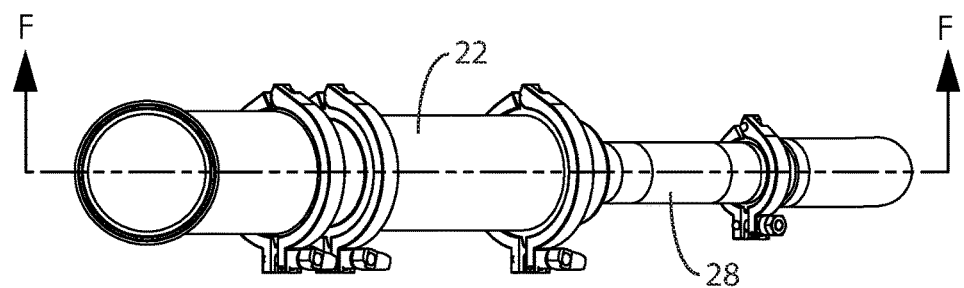
FIG. 6 is a perspective view of the pipeline apparatus of FIG. 1 with the sampling tube in a retracted position.

FIGS. 6-7 show the relationship between fluid cylinder 22 and piston 28. FIG. 7 also illustrates the location of retract fluid inlet 36 and extend fluid inlet 38.

FIGS. 8-10 show apparatus 10 not connected to duct 12. Duct end 24 of fluid cylinder 22 is shown as well as duct-connecting structure 34. FIG. 9 illustrates that sample tube 14 of apparatus 10 has a circular cross-section.

FIGS. 11-12 illustrate sample tube 14 in an extended state and the interaction with piston 28 as well as retract fluid inlet 36 and extend fluid inlet 38.

FIGS. 13 and 15 are similar to FIGS. 8 and 10 except that FIGS. 13 and 15 illustrate sample tube 14 in the retracted position inside fluid cylinder 22. FIG. 14 is identical to FIG. 9 in illustrating that the cross-section of sample tube 14 is circular.

FIGS. 16-17 are similar to FIGS. 11-12 except that sample tube 14 is in the retracted state within fluid cylinder 22 in FIGS. 16-17. FIGS. 16-17 clearly show closed distal end 16 inside duct end of fluid cylinder 24.

Figure 19:
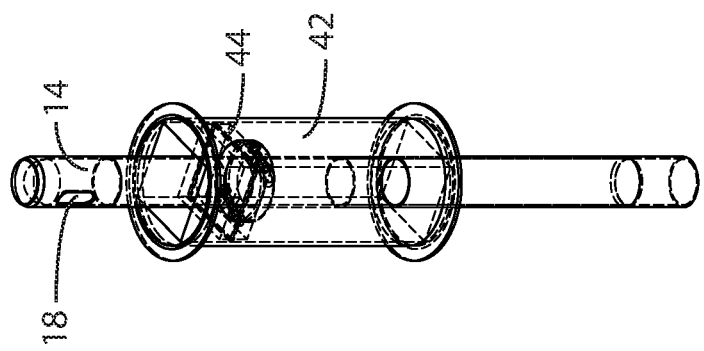
FIG. 19 is a cutaway view of the pipeline apparatus of FIG. 18.
Figure 18:
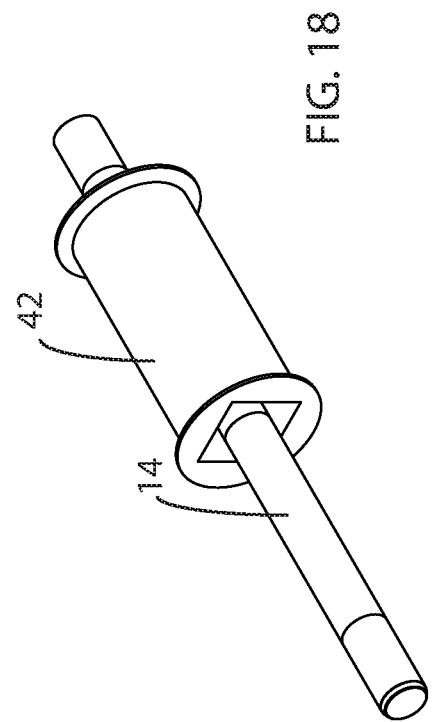
FIG. 18 is a perspective view of a second embodiment of the inventive pipeline apparatus for collecting a dry material sample flowing in a duct.

FIGS. 18-25 illustrate two additional embodiments of apparatus 10, apparatus 10a in FIGS. 18-23 and apparatus 10b in FIGS. 24-25. In embodiment 10 of the inventive apparatus of FIGS. 18-23, piston 44 and fluid-cylinder 42 have non-circular cross-sections, thereby preventing rotation of piston 44 in fluid-cylinder 42. FIGS. 22-23 also illustrate that first and second sealing sleeves may include non-circular seals 40. As illustrated in FIGS. 18-23, non-circular cylinder 42 and piston 44 have a square shape but many other non-circular shapes provide the anti-rotation performance of the inventive apparatus. FIGS. 19-20 illustrate that piston 44 can also be non-circular, such as for example, a square shape or any other non-circular shape.

In FIGS. 24-25, a third embodiment 10b of the inventive apparatus includes a non-circular sample tube (not shown) which in such embodiment will rotate as desired. Apparatus 10b includes a housing end 46 which has a non-circular aperture 46 through which a sample tube having a non-circular cross-section slides, driven by a piston (not shown) and cylinder housing 50. Such piston and cylinder 50 may have simple circular cross-sections since the anti-rotation performance of apparatus 10b is provided by aperture 46 and its mating sample tube. By comparison, apparatus 10 of FIGS. 1-17 includes a circular piston 28 and circular cylinder 22, and anti-rotation performance is provided by the centerline of cylinder 22 not being coextensive with the centerline of sample tube 14.

Wide varieties of materials are available for the various parts discussed and illustrated herein. While the principles of this invention and related method have been described in connection with specific embodiments, it should be understood clearly that these descriptions are made only by way of example and are not intended to limit the scope of the application. It is believed that the invention has been described in such detail as to enable those skilled in the art to understand the same and it will be appreciated that variations may be made without departing from the spirit and scope of the invention.

We claim:

1. An apparatus for collecting a dry material sample flowing in a duct, the apparatus comprising:
    a sample tube having a closed distal end and a sample-inlet aperture in the wall of the sample tube adjacent the closed distal end;
    a housing configured as a fluid cylinder and having a duct end and an opposite outlet end;
    a piston mounted around and connected to the sample tube and positioned within the housing;
    first and second sealing sleeves around and slideably supporting the sample tube, the duct end including the first sealing sleeve and the outlet end including the second sealing sleeve; and
    a duct-connecting structure extending between the duct end of the housing and the duct,
    whereby the sample tube is a piston rod within the fluid-cylinder housing, and the fluid-cylinder housing is configured to extend and retract the sample tube within the duct.

2. The apparatus of claim 1 wherein the fluid cylinder is an air cylinder.

3. The apparatus of claim 1 wherein the duct-connecting structure is welded to the duct.

4. The apparatus of claim 1 wherein the duct end includes a retract fluid inlet to the fluid cylinder.

5. The apparatus of claim 1 wherein the outlet end includes an extend fluid inlet to the fluid cylinder.

6. The apparatus of claim 1 wherein the sample tube and the fluid-cylinder housing have centerlines which are not coextensive.

7. The apparatus of claim 1 wherein the piston and fluid-cylinder have non-circular cross-sections, thereby preventing rotation of the piston in the cylinder.

8. The apparatus of claim 1 wherein the first and second sealing sleeves include non-circular seals and the sample tube is non-circular, configured to sealingly slide within the non-circular seals.

* * * * *